United States Patent [19]

Jackson

[11] Patent Number: 5,103,832

[45] Date of Patent: Apr. 14, 1992

[54] BIOLOGICAL PRESSURE TRANSDUCER ZEROING AND LEVELLING REFERENCE APPARATUS

[75] Inventor: Gregory K. Jackson, Vienna, Va.

[73] Assignee: Gregmed, Hackensack, N.J.

[21] Appl. No.: 596,191

[22] Filed: Oct. 11, 1990

[51] Int. Cl.⁵ .............................................. A61B 5/02
[52] U.S. Cl. .................................. 128/675; 128/748
[58] Field of Search ............... 128/748, 672, 673, 675; 73/4 R, 716

[56] References Cited

U.S. PATENT DOCUMENTS

| | | | |
|---|---|---|---|
| 3,095,872 | 11/1959 | Tolks | 128/672 |
| 4,576,035 | 3/1986 | Hooven et al. | 73/4 R |
| 4,779,626 | 10/1988 | Peel et al. | 128/675 |

OTHER PUBLICATIONS

Corbett et al., "A Self-Levelling Central Venous Eletromanometer", Med. and Biol. Engr., vol. 12, No. 3, 5/74. p. 366.

Blackburn, J. P., "Self-levelling Venous Pressure Transducer", Br. Med. J.; V. 4f825 12/68.

Palley et al., "A computerized System for Routine Cardiac Output Measurements", Proceedings of the 23rd Conference on Eng. in Bio. and Med. 11/70, p. 4.

*Primary Examiner*—Max Hindenburg
*Attorney, Agent, or Firm*—McGlew & Tuttle

[57] ABSTRACT

A medical pressure measurement device which employs a reference transducer linked to an atmospheric pressure sensitive device while also connected in immediate proximity to a single or several pressure measurement transducers which allows for automatic correction for hydrostatic transducer height difference from patient point to reference (usually some point on the patient's external anatomy equivalent in vertical height to the right atrium of the heart) to transducer position; while providing a constant zero pressure reference, i.e., ambient atmospheric pressure to the monitoring device via said reference transducer system.

7 Claims, 3 Drawing Sheets

BIOLOGICAL PRESSURE TRANSDUCER ZEROING AND LEVELLING REFERENCE APPARATUS

BACKGROUND OF THE INVENTION

1. Field of the Invention

The present invention relates to a device which provides an automatic reference point (usually atmospheric pressure) for pressure transducer setups that convert biological pressure signals from various invasive monitoring devices into electrical signals which can then be processed, displayed in various forms using various methods, and(or) stored using various methods.

Current pressure transduction and monitoring systems in use require that the pressure monitoring transducer(s) be connected to the chamber of measurement (e.g. the heart's right atrium, the radial artery, the pulmonary artery, et. al.) via a sealed, ideally non-compliant conduit containing a continuous, uninterrupted line of fluid between the chamber and said monitoring transducer. The fluid is usually 0.9% NaCl in water containing a small amount of the anticoagulant heparin sodium to prevent clotting of the invasive monitoring line. This fluid-containing conduit transmits the pressure impulse from the chamber of measurement to the pressure transducer.

In order that the pressure transduction into the electrical signal not be influenced by the hydrostatic height of the fluid in the conduit, the transducer is usually mounted at the bedside in a fixed position so that it sits at roughly the same horizontal height as the chamber being measured (e.g. the right atrium of the heart). Once set up in this fashion, any artifact due to fluid column height is eliminated. By convention, the hydrostatic height of the right atrium of the heart is generally used as the point of reference for all types of invasive monitoring. Even peripheral arterial lines.

Often, a three-way stopcock is used to temporarily interrupt this fluid continuity and allow the small remaining fluid at the transducer to be exposed to air, hence atmospheric pressure. This maneuver, referred to as "zeroing the transducer," allows, the operator to set the monitoring device to zero during this exposure to air; thus allowing all further pressure measurements once the fluid continuity to body chamber of measurement has been reestablished, to be expressed in relation to atmospheric pressure. This zeroing maneuver is important in that it allows each monitoring channel to be set at zero to match the electrical signal produced by the corresponding pressure transducer when said transducer is exposed to air rather than exposed to the fluid conduit connecting it with the monitoring line transmitting pressure in a bodily chamber.

The present invention provides a method of constant transducer reference with the use of a separate reference transducer and reference chamber thus eliminating the need for precise mounting of monitoring transducers at the level of the chamber of measurement while also providing a constant atmospheric zero reference to the monitoring channels. Such an invention would eliminate the need to "zero the transducer," i.e., expose each transducer to air via a 3-way stopcock while setting each corresponding monitoring channel to zero; during monitor setup and during patient transfer to another monitoring location (e.g. intensive care unit to operating room and back again would require three such setups and monitor zeroing maneuvers).

2. Description of Prior Art

Pressure transducer systems currently in use in clinical and research medicine utilize a variety of methods to convey pressure impulses arising from invasive monitoring devices like indwelling arterial catheters, central venous catheters, pulmonary arterial catheters, and left heart catheters and convert or transduce them into proportional analog and(or) digital electrical signals which can then be processed and(or) displayed on monitoring screens, graph paper, and other information display and recording devices (e.g. U.S. Pat. No. 3,946,724).

Many recent devices disclosed utilize various methods of electrical signal processing (e.g. U.S. Pat. Nos. 4,899,760, 4,890,630, 4,530,3265, & 4,190,886) to provide a more reliable and accurate signal display and analysis. None of these prior art references address the issue of simplification of the process of levelling and zeroing the transducer by providing a more constant external reference.

SUMMARY OF THE INVENTION

It is the object of the invention to provide a means for constant reference between a pressure monitoring transducer and a patient reference chamber (by convention, the right atrium of the heart is usually used as a hydrostatic reference height for all invasive monitoring devices, or an equivalent point on the external anatomy) of pressure measurement while also providing a constant reference with respect to ambient atmospheric pressure, usually set as the zero point for each monitoring channel used corresponding to each pressure transducer's electrical signal when exposed to air, i.e., ambient atmospheric pressure. Such a device would provide accurate zero reference without requiring each transducer to be exposed to air during monitor setup; and regardless of transducer position relative to the patient/reference chamber of measurement by continuously correcting for hydrostatic vertical height differences between the two.

This goal is accomplished by providing a separate reference transducer firmly mounted to the pressure monitoring transducer(s). This reference transducer measures atmospheric pressure at a point on the patient at a hydrostatic height equivalent to the right atrium of the heart via a fluid-containing conduit that attaches to a fluid reservoir sensitive to ambient atmospheric pressure yet able to provide a seal adequate to prevent fluid leakage and(or) entrapment of air into the system. The reservoir which can assume any shape or size able to accomplish the described task of transmitting atmospheric pressure to a fluid conduit; can be connected directly to the patient at a point level with the reference chamber of measurement (by convention, the right atrium of the heart. Hence, an ideal spot of attachment of the atmospheric pressure measurement reservoir might be somewhere on the upper arm or shoulder).

The provision of a reservoir in accordance with the invention provides a stable reference point whose height can be measured in relationship to the reference transducer based on pressure transmitted to the transducer (e.g. when the reference transducer rests above said mounted reservoir and patient, a negative pressure is transmitted to the transducer and when it rests below said mounted reservoir and patient, a positive pressure is transmitted to the transducer). This reference signal produced by this additional reference transducer can be subtracted from the signal produced by each channel connected to the actual pressure monitoring transducer(s). The resultant signal(s) contains no hydrostatic fluid-height artifact as this has been corrected for using the reference transducer, and hence, there is no need to mount monitoring transducers at a precise height in fixed position at the bedside or even to secure them in a stable position; since the reference transducer will continuously allow for correction in variations monitoring transducer height.

Additionally, by exposing the reservoir to ambient atmospheric pressure (e.g. via a watertight but loose membrane), said reference transducer (also connected to said reservoir by a low compliance fluid conduit) provides a constant zero reference to the monitoring device, thereby eliminating the need for time consuming "zeroing" (exposing each transducer to air via a 3-way stopcock while the corresponding monitoring channel is set to zero) maneuvers that also interrupt monitoring.

These two attributes of the device according to the invention allow for faster patient transfer to different monitoring areas (e.g. operating room to intensive care unit, etc.), easier organization of monitoring lines (transducers can be neatly tucked out of the way without regard to specific position, and even mounted in a more sleek fashion, at any convenient distance from the patient), and time saved by elimination of the need to "zero the transducer" which can interrupt monitoring at crucial clinical moments. It is an object of the invention to allow for precise, accurate, and uninterrupted measurement of pressure in various intravascular chambers with elimination of the need for stable, and horizontally level mounting of transducers in relation to the patient.

It is a further object of the invention to eliminate time spent in patient transfer zeroing monitor channels to atmospheric pressure (by opening up pressure transducers to air via a 3-way stopcock) and monitoring transducers at a stable and horizontally "correct" height.

It is a further object of the invention to simplify the setup required in patients undergoing aforementioned types of invasive monitoring. There is no need to mount transducers in a stable position at the bedside and hence, this allows for more compact, unified banks of transducers that can be placed anywhere and be subject to movement, table or bed adjustments, and patient movement without loss of accuracy.

According to the invention, an additional reference transducer is provided that is firmly mounted to the monitoring transducer(s). This reference transducer connects to a fluid chamber via a fluid containing conduit (the fluid of the same density as that in the other transducer conduits) resulting in an uninterrupted connection between said fluid chamber and said reference transducer. The conduit is preferably composed of a non-compliant material so that it will transmit pressure changes rather than absorb them. The fluid chamber preferably attaches to the patient at a standard point of pressure reference (by convention the right atrium of the heart, for all intravascular types of monitoring, hence attachment to the upper arm or chest via any appropriate means such as adhesive backing or via a strap would serve as an adequate reference point). This fluid chamber should be capable of transmitting ambient atmospheric pressure to the contained fluid. One such means might comprise a sealed flexible membrane.

The resulting system would produce the following results:

When the reference transducer sits at the same horizontal level as the mounted fluid reservoir, atmospheric pressure is transmitted to the transducer. When said reference transducer falls below the level of said mounted fluid reservoir, atmospheric pressure plus positive fluid hydrostatic pressure is transmitted. When said reference transducer rises above the level of said mounted fluid reservoir, atmospheric pressure plus negative fluid hydrostatic pressure is transmitted. All such pressures are converted to electrical signals in either digital or analog fashion via the reference transducer.

In processing the resultant electrical signal that reaches the monitoring device, as long as all other measurement transducers are physically attached in immediate proximity to said reference transducer (and essentially identical in transduction properties), the monitoring device receiving the electrical signals can simply subtract the electrical signal produced by the reference transducer from the electrical signal(s) produced by each monitoring channel connected to each pressure transducer, hence correcting for transducer height (e.g. when above the patient, subtraction of a negative value, when below the patient, subtraction of a positive value). This eliminates the need for maintaining a stable and horizontally correct transducer height.

In addition, the monitoring device can effectively use the signal from the reference transducer as its zero point since the mounted fluid chamber it attaches to (via a non-compliant fluid conduit) is exposed to ambient atmospheric pressure (the zero point of most pressure monitoring devices currently in use). This eliminates the need for "zeroing the transducer(s)", i.e., opening each to air via a 3-way stopcock-type valve and adjusting the corresponding monitor channel setting to the zero point.

Said mounted fluid reservoir can be attached to the patient with a variety of means and can comprise a variety of forms capable of transmitting atmospheric pressure to the fluid contained therein.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DETAILED DESCRIPTION OF THE PREFERRED EMBODIMENT

Figure 1:
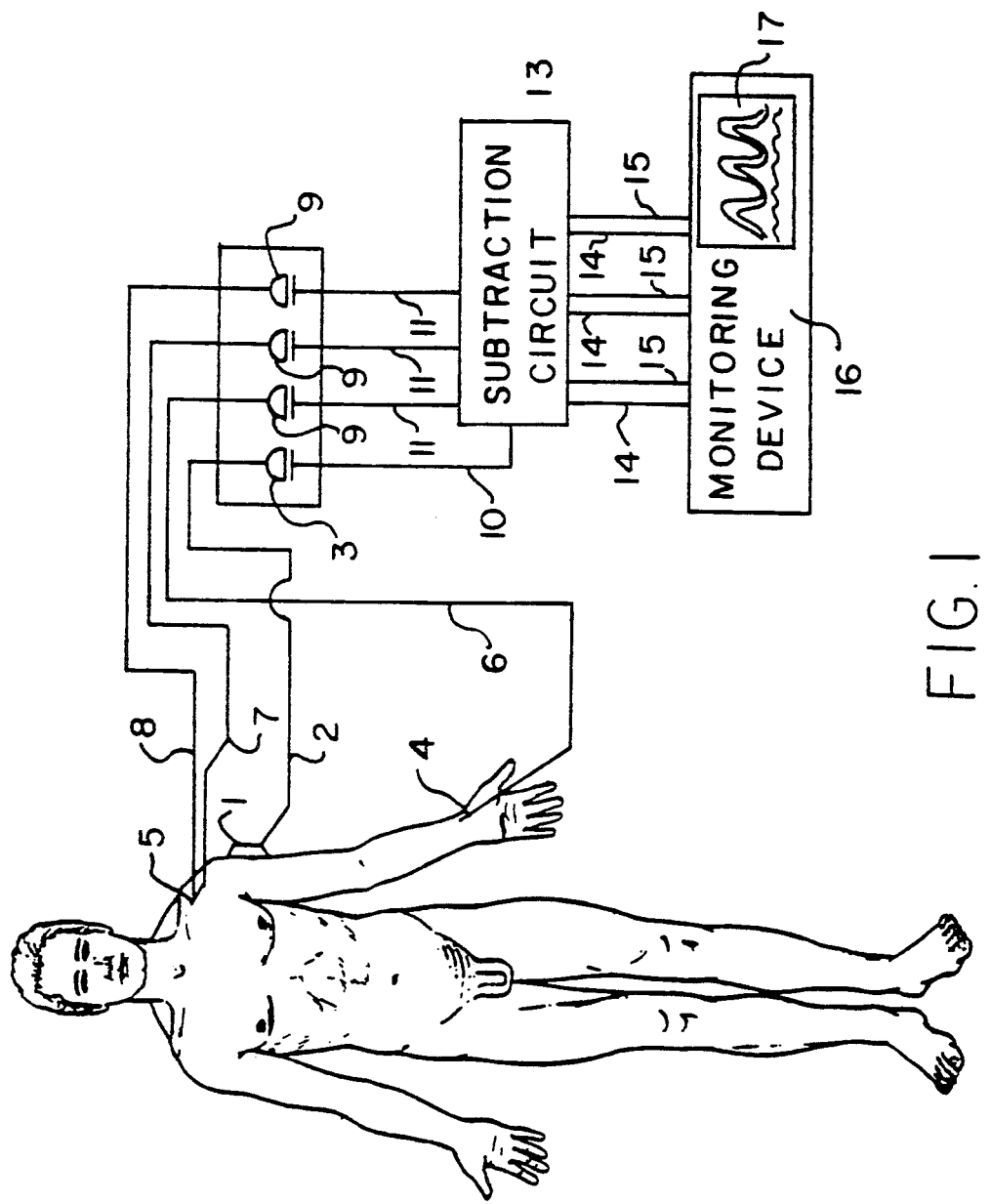
FIG. 1 is a schematic view showing a possible arrangement of 3 monitoring transducers and one reference transducer including the subtractive processing of the reference signal and the provision of a constant zero reference signal for each monitoring transducer channel. In this figure, three such channels are depicted but it is understood that the number of channels used can range from one to several.

Referring to the drawings in particular, the invention embodied therein comprises a biological pressure measurement transducer system, including a biological pressure transmission means generally designated 20 for transmitting pressure of a biological fluid under investigation through a medium to a transducer location 12. A biological pressure transmission means may be in the form of a flexible monitoring line 7, which is filled with a medium such as a fluid which usually comprises the form of 0.9%NaCl in water containing a small amount of the anticoagulant, heparin sodium to prevent clotting of the invasive monitoring line. These fluid-containing conduits 6-8 transmit the pressure impulses from corresponding intravascular chambers of measurement to the transducer location 12. In the example shown in FIG. 1, a pulmonary artery line is inserted in the patients left subclavian vein 5 and is capable of transmitting both pulmonary artery pressure (via fluid-filled monitoring line 8), and central venous pressure (via fluid-filled monitoring line 7) to two separate transducers 9 positioned at the transducer location 12. In addition, a left radial artery cannula 4 transmits arterial pressure, via fluid-filled monitoring line 6, to another transducer 9.

Monitoring transducers 9 can range in number from one to several and are all connected together in immediate proximity by transducer support or connection device 12. The transducers 9 produce analog or digital electrical signals corresponding to the instantaneous pressure level of the medium in the biological pressure transmission means 20, either line 6, 7 or 8. Each of these biological pressure transducers 9 converts a biological pressure impulse to an electrical signal representing the instantaneous pressure level at the transducer location.

An atmospheric pressure transmission arrangement or atmospheric pressure transmission means 35 is provided for compensating for changes in the transducer location. The atmospheric pressure transmission means 35 preferably includes a mounted fluid reservoir 1 connected to a pressure conduit 2. Pressure conduit 2 and the reservoir 1 are supplied with an appropriate second medium which may be identical to the usual 0.9%NACL water solution. However, it is not necessary to provide the same 0.9%NACL water solution and of course it is not necessary to employ an anti coagulant such as heparin sodium as the fluid medium in the atmospheric pressure transmission means 35 will not come in contact with the patient, as long as this fluid comprises the same density as the fluid contained within the other conduit.

Reference transducer means 3 senses atmospheric pressure conveyed by mounted fluid chamber 1 plus (or minus) the hydrostatic effect of height difference between chamber 1 and connection device 12 produced by the fluid in conduit 2 converting it to an electrical digital or analog reference signal.

As can be seen in FIG. 1, the transducer connection device 12 connects each of the transducers 9 and the atmospheric pressure transducer 3 in close proximity and acts to support these transducers at substantially the same level or hydrostatic height.

Each of the transducers 9 convert a pressure impulse to an electrical signal that is conveyed via electrical lines 11 while the reference transducer 3 outputs an electrical signal via electrical line 10. These electrical signals correspond to the instantaneous pressures measured and in the case of transducers 9, correspond to the instantaneous pressure level of the medium at the transducer 9. In the case of reference transducer 3, the electrical signal supplied to electrical line 10 represents the instantaneous pressure of the second medium or medium in conduit 2 measured at the transducer 3. The signals from lines 10 and 11 are supplied to subtraction circuit means 50 which includes a substraction circuit 13 which subtracts the signal from line 10 from each of the signals supplied to lines 11. The resulting values are each transmitted to monitoring device 16 via electrical lines 14.

In addition, the electrical signal carried by electrical line 10 from the reference transducer 3 is passed by electrical conduit 15 to monitoring device 16 where it serves as a constant zero reference for each monitoring channel. Display 17 represents one form of displaying data which results from the system according to this invention. This data may be displayed using graph paper, an LCD screen or a CRT screen or the like.

Figure 2:
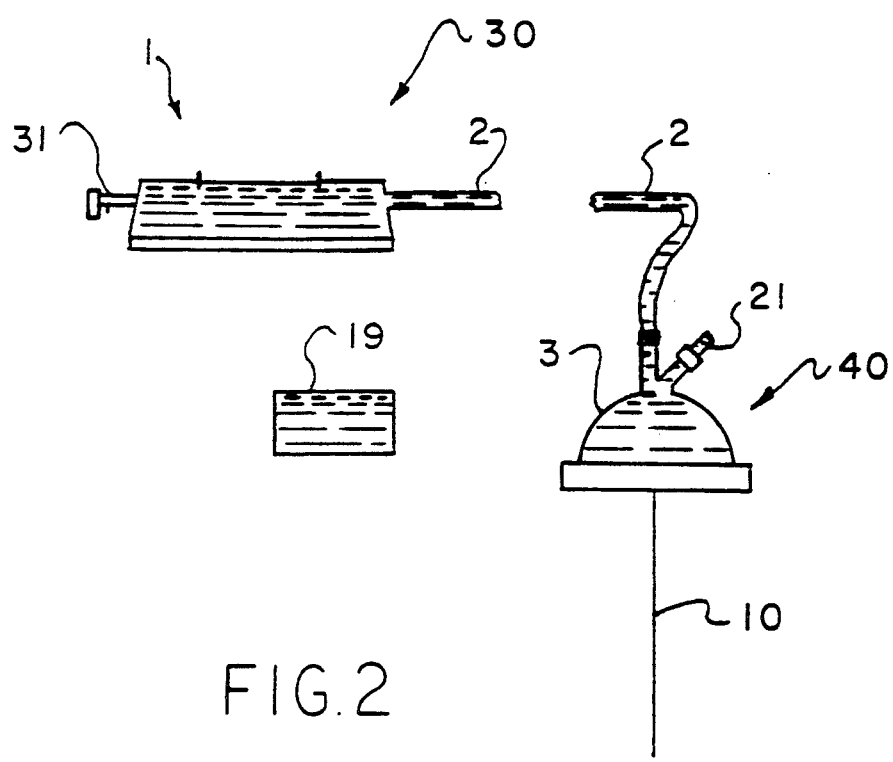
FIG. 2 is a view showing one possible embodiment of said mounted fluid reservoir sensitive to ambient atmospheric pressure and connected to said reference transducer via a low compliance, fluid-containing conduit.

FIG. 2 shows a preferred form of the atmospheric pressure transmission means 30 and the reference pressure transducer means 40. As seen in FIG. 2, the reservoir 1 is provided which includes a housing structure supporting membrane 18. Membrane 18 is impermeable to the second fluid medium but is loose enough to capably transmit ambient atmospheric pressure to the second fluid medium position within the fluid reservoir 1 and loose enough to correspond to the maximum possible deflection of the pressure measurement surfaces contained within said transducers. The fluid filled monitoring line 2 is connected to the reservoir 1 and this fluid filled monitoring line is in turn connected to the reference transducer 3. A valve 21 is provided cooperating with the reference transducer 3 and a valve 31 is provided cooperating with the reservoir 1 to allow second fluid medium 19 to be filled during setup allowing air to escape.

The reservoir 1 is substantially preferably positioned on or near the body of the patient at a point equivalent in hydrostatic height to the right atrium of the heart. According to another aspect of the invention, an adhesive member 20 is provided on a lower side of the reservoir 1 for adhering the reservoir to the patient.

Figure 3A:
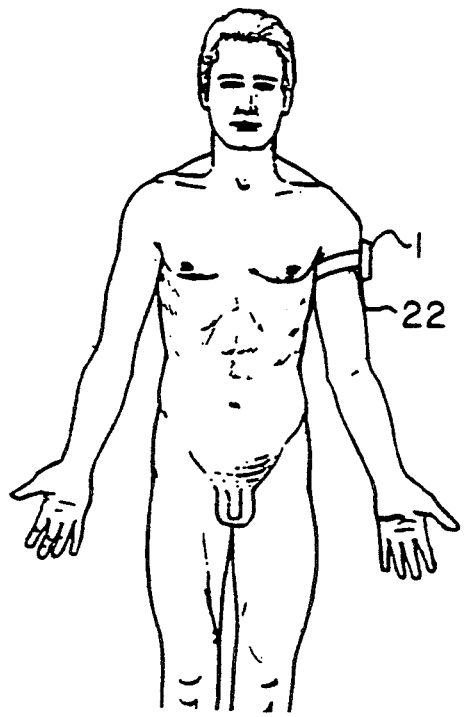
FIGS. 3a and 3b depict alternate methods of mounting said fluid reservoir at hydrostatic heights equivalent to the right atrium of the heart.
Figure 3B:
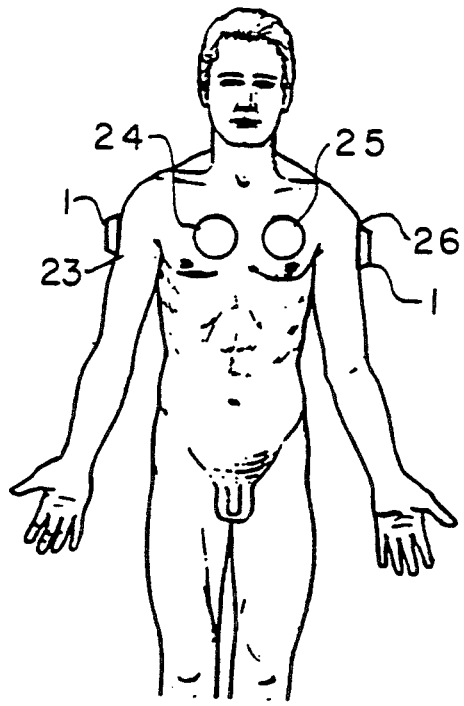

FIG. 3 A and B show various locations and methods for mounting fluid reservoir 1 to the patient at a point substantially equivalent in hydrostatic height to the right atrium of the heart. Locations 23 through 26 employ the use of the adhesive to backing 20 for fixing the location of the reservoir 1. As seen in FIG. 3A, the reservoir 1 may also be strapped to the patient using strap 22 though any feasible mode of attachment will serve the same purpose.

In operation, no initial zeroing is required since the channel connected to the reference transducer is always set to represent zero. In addition, any changes in pressure in the signals generated by monitoring transducers 9 due to changes in hydrostatic height are offset by the signal from reference transducer 3. Of course if the transducer connection device is maintained at a position of equal hydrostatic height to the right atrium and hence, to the mounted fluid reservoir, no value will be subtracted from the signals output by the transducers 9.

While a specific embodiment of the invention has been shown and described in detail to illustrate the application of the principals of the invention, it will be understood that the invention may be embodied otherwise without departing from such principals.

What is claimed is:

1. A biological pressure measurement transducer system, comprising:
   biological pressure transmission means for transmitting biological fluid under investigation, to a transducer location;
   biological pressure transducer means for sensing an instantaneous pressure level of said biological fluid at the transducer location and generating a biological pressure signal representing the instantaneous pressure level at the transducer location;
   atmospheric pressure transmission means for transmitting atmospheric pressure, from a location adjacent a patient, through a medium to the transducer location;
   reference pressure transducer means for sensing an instantaneous pressure level of said medium at said transducer location and generating a medium transducer location pressure signal representing said medium instantaneous pressure level at said transducer location;
   transducer connection means for supporting said biological transducer means and for supporting said reference transducer means at a vertical height substantially equal to a vertical height of said biological pressure transducer; and,
   substraction circuit means for subtracting said medium transducer location pressure signal from said biological pressure signal.

2. A biological pressure measurement system according to claim 1, wherein said atmospheric transmission means includes a reservoir filled with said medium including a flexible but impermeable membrane that effectively conveys atmospheric pressure to said medium and transmitted to said reference pressure transducer through a conduit connected to said reservoir and filled with said medium.

3. A biological pressure measurement system according to claim 2, wherein said reservoir includes connection means for attaching said reservoir to a patient for fixing the reservoir at a horizontal level substantially equal to a horizontal level of a biological chamber being monitored.

4. A biological pressure measurement transducer according to claim 3, wherein said connection means includes a self-adhesive backing positioned on said reservoir.

5. A biological pressure measurement system according to claim 3, wherein said connection means includes a strap connected to said reservoir.

6. A biological pressure measurement system according to claim 1 further comprising means for displaying said signals output by said substraction circuit means.

7. A biological pressure measurement system according to claim 1, wherein said medium has substantially the same density as said biological fluid.

* * * * *